(12) United States Patent
Yano

(10) Patent No.: US 6,426,510 B1
(45) Date of Patent: Jul. 30, 2002

(54) DEVICE AND METHOD FOR INSPECTING PATTERN SHAPES

(75) Inventor: Jun-Ichi Yano, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/456,272

(22) Filed: Dec. 7, 1999

(30) Foreign Application Priority Data

Dec. 7, 1998 (JP) .......................................... 10-347148

(51) Int. Cl.[7] ........................ G01N 21/88; G01N 21/00
(52) U.S. Cl. ................................ 250/559.48; 356/237.5
(58) Field of Search .................. 250/559.48; 356/237.5, 356/237.2

(56) References Cited

U.S. PATENT DOCUMENTS

| 3,908,118 A | * | 9/1975 | Micka | ............................. 716/4 |
| 5,838,433 A | * | 11/1998 | Hagiwara | .................... 356/364 |

FOREIGN PATENT DOCUMENTS

| JP | 63-125047 | 5/1988 |
| JP | 63-56702 | 11/1988 |
| JP | 2-266755 | 10/1990 |
| JP | 3-34774 | 2/1991 |
| JP | 4-362789 | 12/1992 |
| JP | 5-76005 | 3/1993 |
| JP | 11-185041 | 7/1999 |

\* cited by examiner

Primary Examiner—Stephone Allen
Assistant Examiner—Eric Spears
(74) Attorney, Agent, or Firm—Scully, Scott, Murphy & Presser

(57) ABSTRACT

An inspection device for inspecting pattern shapes of rectiles or mask patterns is disclosed. The inspection device includes a light source for irradiating inspection light, a scanning unit for scanning the inspection light, an inspection light dividing unit for dividing the inspection light scanned by the scanning unit, a monitor light detecting unit for receiving one of the inspection lights divided by the inspection light dividing unit and converting the one of the inspection lights to a monitor signal, a transmitting light detecting unit for receiving a transmitting light, which has transmitted through a pattern shape, among the other inspection lights divided by the inspection light dividing unit and converting the transmitting light into a transmission detecting signal. The inspection device further comprises a waveform shaping unit for removing an alternate current component, within a primary scanning time period of the scanning unit, of monitor signals outputted from the monitor light detecting unit at each round of the primary scanning to convert the monitor signals into a rectangular-shaped wave of an approximately constant value, and a first correction unit for dividing the transmission detecting signal by the rectangular-shaped wave, which has undergone shaping in the waveform shaping unit, as a divisor group, and a second correction unit for dividing the transmission detecting signals corrected in the first correction unit with predetermined reference transmitting signals as a divisor group and outputting the results of said division as an inspection image.

10 Claims, 8 Drawing Sheets

DEVICE AND METHOD FOR INSPECTING PATTERN SHAPES

BACKGROUND OF THE INVENTION

1. Field of the Invention

The present invention relates to a method for inspecting pattern shapes, and improvements in a device therefor.

2. Description of the Prior Art

The manufacturing process of a semiconductor device includes a process in which necessary patterns are transferred on a substrate with a mask pattern (reticle) comprising a shielding portion and a transparent portion. Accuracy of the transferred pattern image by the mask pattern significantly influences the performance of a semiconductor device, and thus it is required that a highly accurate pattern image is transferred by the mask pattern.

Conventionally, the method for inspecting the transferred pattern image by the mask pattern is disclosed in Japanese Patent Publication No. B63-56702 specification, etc. In this conventional example, existence of abnormality in a pattern to be inspected is detected by comparing an inspection image which has been picked up by irradiating a laser beam to the pattern to be inspected with designed data.

However, this conventional example has disadvantages in that changes of a laser light source due to the lapse of years or variations of scanning means to scan the surface of a pattern to be inspected with a laser beam may give rise to variation in optical intensity of the inspection light, and thus the optical intensity profile of scan transmitting light within a scanning range may change, or holistic intensity drops may cause the entire gradation of an inspection image to become unusable.

Consequently, the inspection accuracy of the mask pattern may decrease.

In addition, when using the diffraction effect of an acousto-optic element as scanning means, the diffraction effect varies in accordance with the temperature of the acousto-optic element, and consequently, the optical intensity per process area may vary. This variation in optical intensity due to the temperature of the scanning means is generated mainly in a sub-scanning direction. In addition, also as for a primary scanning direction, the optical intensity may vary within a primary scanning time period (e.g., 6 $\mu$sec. according to changes in the configuration of the optical system,.

BRIEF SUMMARY OF THE INVENTION

Object of the Invention

An object of the present invention is to reduce the disadvantages which such conventional examples have, and especially, even though there are variations in the optical intensity of a laser beam, to remove influence from this variation components and thus maintain inspection accuracy.

Moreover, another object of the present invention is to remove the influence of both variation in the optical intensity in the primary scanning direction of a laser beam and variation in the optical intensity in the sub-scanning direction thereof, maintain inspection accuracy even though there are changes due to the lapse of years or changes in temperature, and thereby improve the yield factor of semiconductor products.

In addition, another object of the present invention is to maintain this inspection accuracy at low costs, as well as at a high speed and in a stable manner.

SUMMARY OF THE INVENTION

The present invention comprises a light source of irradiating inspection light, a scanning unit for scanning the inspection light, an inspection light dividing unit for dividing the inspection light scanned by the scanning unit, a monitor light detecting unit for receiving a part of the inspection light divided by the inspection light dividing unit and converting it to a monitor signal, a transmitting light detecting unit for receiving a transmitting light, which has transmitted through a pattern shape, and converting the transmitting light into a transmission detecting signal, a waveform shaping unit for removing an alternate current component, within the primary scanning time period of the aforementioned scanning unit, of monitor signals outputted from the monitor light detecting unit at each round of the primary scanning to convert the monitor signals into a rectangular-shaped wave of an approximately constant value.

Moreover, the present invention further comprises a first correction unit for dividing the transmission detecting signal by the rectangular-shaped wave, which has undergone shaping in the waveform shaping unit, as a divisor group, and a second correction unit for dividing the transparent detecting signals corrected in the first correction unit with predetermined reference transmitting signals as a divisor group and outputting the results of said division as an inspection image.

Here, the inspection light is divided, and one part is treated as the monitor signal and the other part is treated as the inspection light. And the inspection light transmits the pattern shape such as reticle or mask pattern, etc. The pattered portion shields lights, and thus the transmitting light will represent the shape of the pattern. In general, among pattern shapes the portion not patterned is a glass surface, and thus the inspection light transmits through the glass surface to become a transmitting light.

Depending on the primary scanning direction, intensity of the transmitting light undergoes slight changes. This is caused by changes in intensity of the inspection light due to scanning angle of the scanning unit, and changes in intensity of the transmitting light as a result of transmitting through an optical system. For the purpose of correcting the changes in intensity which appear in this primary scanning direction every time, a pattern shape configured with only glass surface without comprising any pattern in advance and the like should be equipped and the transmitting reference signal should be measured. The second correction unit divides the transmission detecting signal by the transmitting reference signal, and thus corrects changes in intensity appearing in the primary scanning direction every time.

In addition, the optical intensity of the inspection light varies in the sub-scanning direction as well. For example, where the scanning unit and the inspection light dividing unit are temperature-dependent, intensity of the inspection light varies in the sub-scanning direction in accordance with changes in temperature. In addition, it is expected that the output of the light source will be changed after the transmitting reference signal has been measured. For purpose of removing such variation of optical intensity of the transmitting light appearing during a period longer than the time range of primary scanning, the first correction unit divides the transmission detecting signal with the monitor signal. Then, for the variation of optical intensity in the sub-scanning direction, if any, the transmission detecting signal and the monitor signal vary at the same ratio, and therefore, dividing-calculation results will remain constant.

And at this time, the correction purpose in the first correction unit occurs during a period longer than the primary scanning period, the waveform shaping portion removes the alternate current components during the period of one round of the primary scanning from the monitor signal, and leaves only the direct current components. In particular, for example, the peak within a short time period δt-immediately after the monitor signal rises is maintained, and this peak value is outputted during the period of the said one round of primary scanning. In addition, using this approximately rectangular-shaped monitor signal, the first correction unit implements dividing-calculation, and thus only the level of transmitting signal appearing in the sub-scanning direction can be corrected. In addition, the monitor signal is shaped into a rectangular-shaped wave so that it is not subject to the influence of the optical intensity which takes place only in the monitor signal during the primary scanning period immediately after the inspection light has been divided. Especially, in spite that the fracture takes place at the time of trailing of the monitor signal, the level of the transmission detecting signal can be corrected without being influenced by this fracture. On the other hand, using the transmitting reference signal having transmitted through the glass surface, the second correction unit is corrected, and thus the variation components of the transmission detecting signal appearing in the primary scanning direction can be removed under the state including the variation of the optical intensity due to transmitting through the glass surface.

DETAILED DESCRIPTION OF THE PREFERRED EMBODIMENTS

Embodiments of the present invention are described in detail with reference to the drawings as follows.

Figure 1:
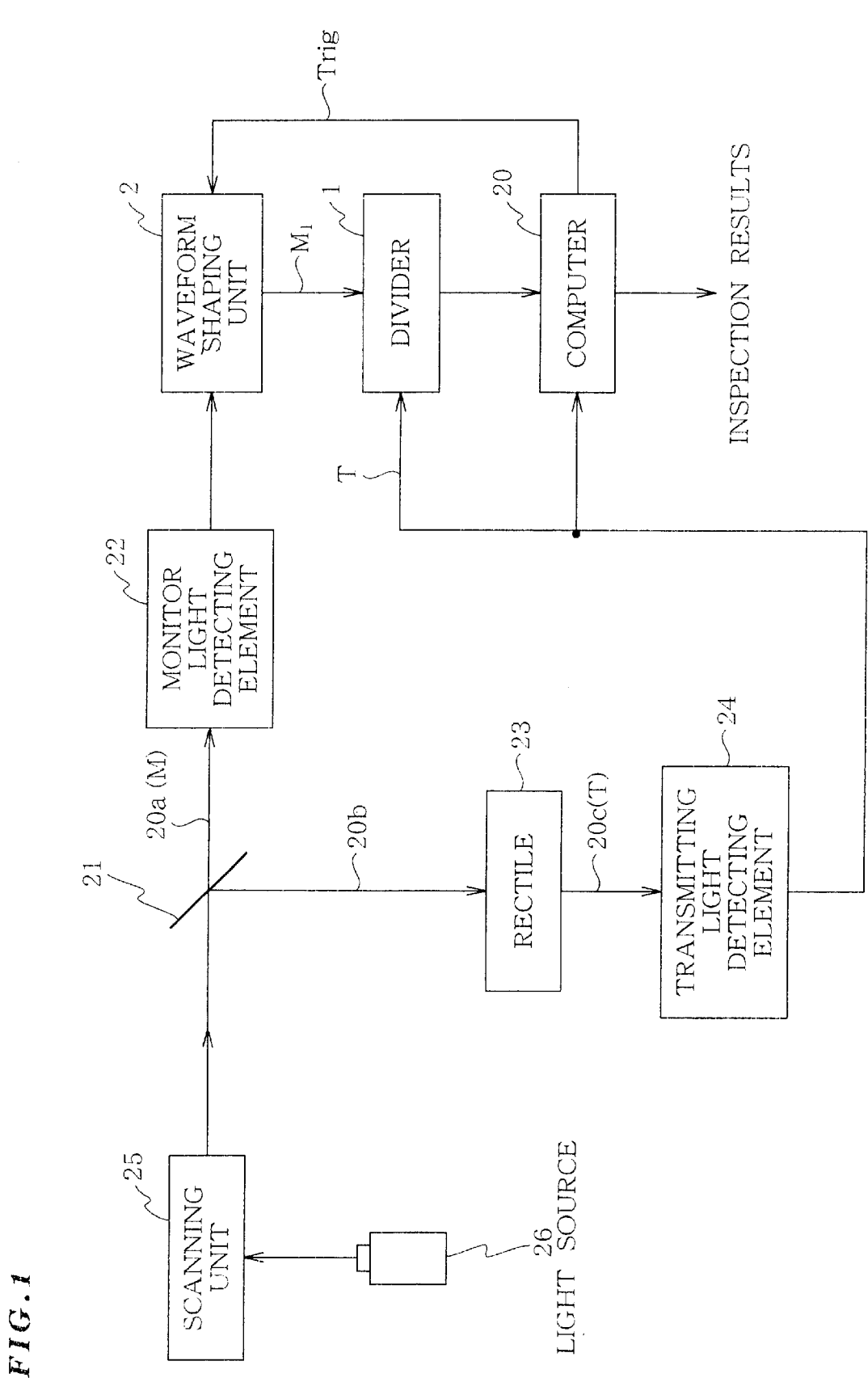
FIG. 1 is an explanatory view showing a configuration example of an embodiment of the present invention.

With reference to FIG. 1, the pattern shape inspection device according to the present invention comprises a light source 26 irradiating the inspection light, a scanning unit 25 for example comprising an audio optical element to scan the inspection light, an inspection light dividing unit 21 dividing the inspection light which has been scanned by this scanning unit 25, a monitor light detection unit (monitor light detection element) 22 receiving one part of the inspection light 20a having undergone division by the inspection light dividing unit 21 to convert into the monitor signal M, and a transmitting light detecting unit 24 receiving the light having passed through the pattern shape (such as mask pattern and reticle, etc.) 23 to convert to transmission detecting signal T.

Figure 2:
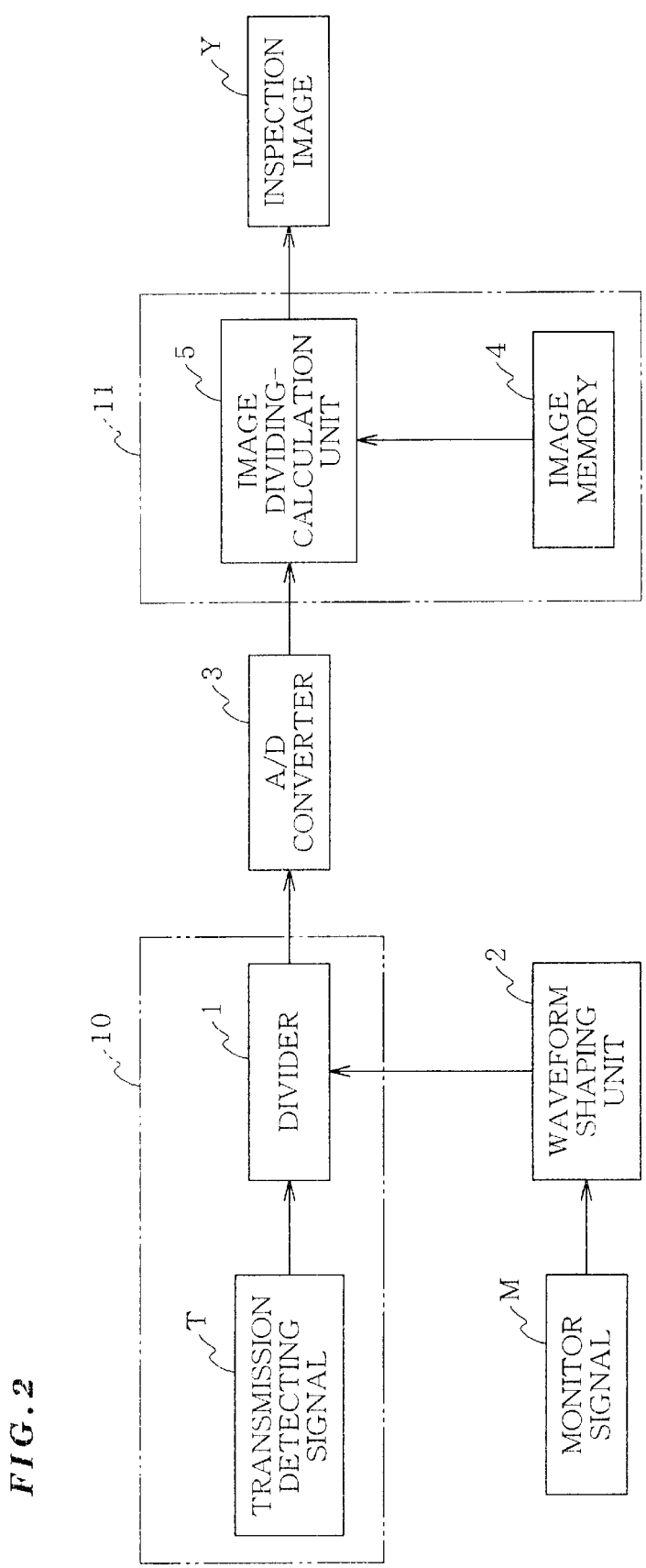
FIG. 2 is a block diagram showing a detailed configuration of a computer shown in FIG. 1.

With reference to FIG. 2, the pattern shape inspection device further comprises a waveform shaping unit 2, a first correction unit 10, and a second correction unit 11, wherein the waveform shaping unit 2 removes the alternate current component within the primary scanning time period by the aforementioned scanning unit among monitor signals M outputted form the monitor light detecting unit at each round of the primary scanning to convert to the rectangular-shaped wave M1 of an approximately constant value, the first correction unit 10 divides the aforementioned transmission detecting signals with the rectangular shape waves M1 as divisor group adjusted by this waveform shaping unit 2, and the second correction unit 11 divides this transmission detecting signal T2 having been corrected in this first correction unit 10 with the predetermined reference transmitting signals Z as divisor group as well as outputs the results of division as an inspection image Y.

The inspection light dividing unit 21 can be realized by for example a half mirror (partially reflecting mirror) 1. In the example shown in FIG. 1, the inspection light 20 is divided into two parts, a part of the inspection light 20a is received with the monitor light detecting element 22 and obtained as a monitor signal M containing variation component Ti of the opto-intensity prior to arrival to the reticle 23, and another part at the inspection light 20b is irradiated to the reticle 23, and the light having passed through the transmission unit of the reticle 23 is received with the transmitting light detecting element 24, and this is obtained as the transmission detecting signal T.

The first correction unit 10, in the examples shown in FIG. 1 and FIG. 2, comprises a divider 1 which divides one value with the other when two analog signals are inputted, and outputs in succession the outcome of the division. In the examples shown in FIG. 1 and FIG. 2, the first correction is implemented under the state of analog signal, and the second correction is implemented under the state of digital signal. Therefore, A/D converter 3 is comprised to convert the transmission detecting signal T2 after the first correction being the output on the divider into digital data.

The waveform shaping unit 2 extracts only the direct current components of the monitor signal M to shape into rectangular-shaped waveform. In the example shown in FIG. 1, since the alternate current components of the monitor signal M must be removed on a real time basis so that the division should be implemented with an analog circuit, the output from the waveform shaping unit 2 is not always a rectangular wave. But the waveform shaping unit 2 outputs the monitor signal M1 which will be nearly a constant value under the status covering the entire primary scanning period.

In the example shown in FIG. 1, the inspection light is divided, and one monitor signal M is not transmitted through the pattern shape, but the other inspection light is transmitted through the pattern shape, and moreover, the transmission detecting signal is divided by the monitor signal M as a divisor. Thus, even if the optical intensity of inspection light itself is varied, the monitor signal M and the volume of transmission detecting signal varies at the same ratio as the increase in optical intensity of that inspection light, thus taking the division thereof removes the influence due to changes in the optical intensity of the inspection light itself. That is, the transmission detecting signal can be standardized at a constant gradation range. Thus, when the image processing at the last stage is implemented with digital data, even if the optical intensity of the inspection light itself varies, without the maximum value of the transmission detecting signal varying, data covering the whole gradation range available for use can be obtained, and accordingly, the image processing capacity can be used to the maximum extreme. Despite the diffraction effect of the acousto-optic element depending on temperature, and the changes in temperature has given rise to the intensity of the inspection light for a process area, this makes it possible to remove the influence due to that change, and to implement the inspection on shape with a constant accuracy.

Moreover, in the present embodiment, the waveform shaping unit 2 removes the alternate current unit T1 of the monitor signal M1. When the value of the monitor signal M1 will become approximately stable at a constant, the divider will proceed with dividing approximately at a constant value. Then, regardless of the frequency characteristics of the divider, stable dividing results can be obtained, and accordingly, the configuration shown in FIG. 1 at low costs without using an expensive divider with good frequency characteristics can be realized.

In addition, after the inspection light is bisected, the light path of the monitor signal and the light path of the transmitting signal are different, and thus, the phenomena such that the alternate current component is overlapped only on the monitor signal, and the level drop called fraction in the trailing edge of the monitor signal takes place are known. When noises give rise to a difference between the waveform of the monitor signal and the waveform of the transmission detecting signal after bisection of the inspection light, the dividing results will not be correct. In the present embodiment, even if thus diffraction has taken place in the monitor signal, and noises corresponding with the light path features of the monitor signal have been overlapped, these noise components appear in the monitor signals as alternate current component, the influence of the noises can be removed. That is, in the present embodiment, it is not necessary to get the strictly same status of the light path of the monitor signal as the light path of the transmitting light. This point is also a factor for low-cost operations.

On the other hand, the waveform shaping unit 2 shapes the monitor signal into a rectangular wave, thus noises having overlapped on the transmission detecting signal due to variation of the optical intensity during a single primary scanning period cannot be removed with the first correction unit 10. This variation of the optical intensity during a single primary scanning period is mainly a variation depending on changes in scanning angles. This variation of the optical intensity includes variation due to transmitting through glass surface such as reticle 23, etc. This variation of the optical intensity due to transmitting through the glass surface is caused by the features of the transmitting portion of the reticle, etc. and is inherent to the reticle.

In addition, there exist noises depending on the light path from the light source to the transmitting light detecting element 24. In the present embodiment, this variation component of the optical intensity during a single primary scanning period is removed with the second correction unit 11. That is, the reference transmitting signal is measured in advance and the transmission detecting signal is divided by this reference transmitting signal, thereby the alternate current components of the transmission detecting signal based on the variation of the optical intensity during a single primary scanning period are removed.

Figure 3:
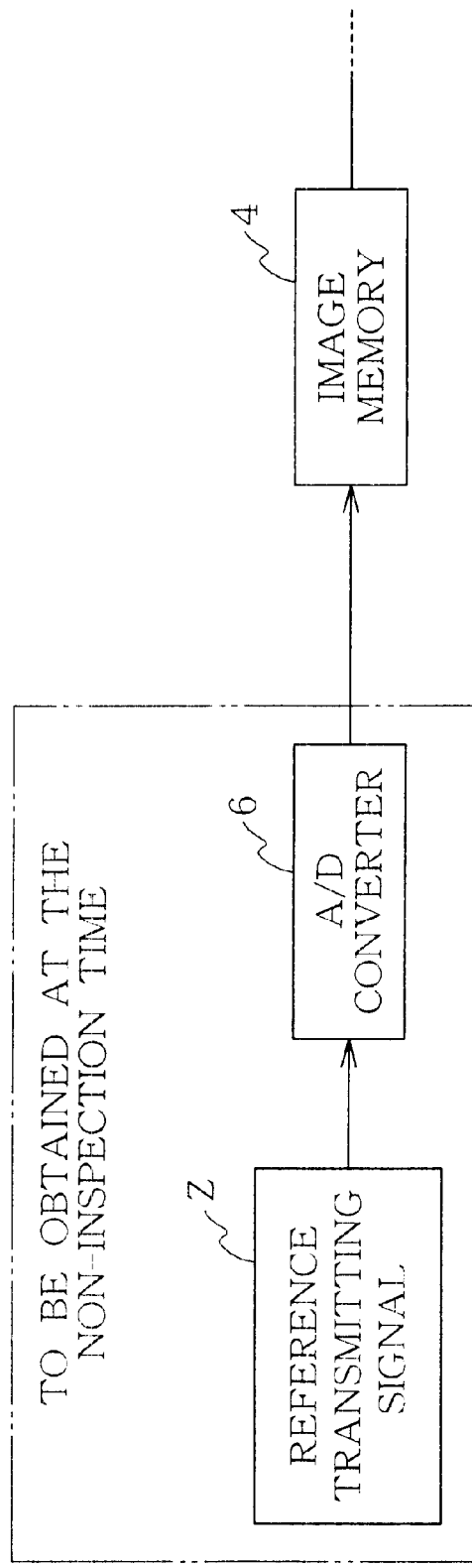
FIG. 3 is a block diagram showing a configuration example to measure the transparent reference signals.

With reference to FIG. 3, to obtain the reference transmitting signal Z, the second correction unit 11 may well comprise the A/D converter 6 to convert to digital data the transmitting reference signal which has transmitted along the same light path as that of the transmission detecting signal and through the glass surface such as reticle, etc. at the time of inspection and the image memory 4 to memorize this transmitting reference signal. That is, the reference transmitting signal Z is obtained based on either of the inspection light 20b which has transmitted through a transparent spot other than a patterned portion (shielding portion) of the reticle 23 before the inspection image is obtained, or the inspection light 20b which has transmitted through an oblique spot other than a shielding portion of the reticle 23. Updating this transmitting reference signal per a constant time period or per a constant rounds of inspection, the variation component of the optical intensity during the primary scanning period can be well removed.

In the examples shown in FIGS. 1 through 3, the first correction unit standardizes the level changes due to the changes in the inspection light intensity to fall within a constant intensity range or a gradation range, and subsequently, the second correction unit removes the alternate current components of variation component of the optical intensity during a single primary scanning period due to scanning angles. That is, the level of the transmission detecting signal is corrected by the first correction unit, and the waveform thereof is shaped by the second correction unit. And, the first correction unit 10 removes influence due to the variation of the optical intensity taking place in the sub scanning direction, and the second correction unit 11 removes influence due to the variation of the optical intensity in the primary scanning direction. Operation of these the first correction unit and the second correction unit makes highly accurate inspection image Y obtainable at comparatively low costs in the present embodiment.

In addition, in an example where the divider is an analog circuit, the waveform shaping unit 2 may well comprise a peak hold circuit which outputs a peak value throughout a predetermined primary scanning time period immediately after the primary scanning of the inspection light starts. This serves to make it possible to convert the monitor signals into rectangular waves on a real time basis.

Figure 4:
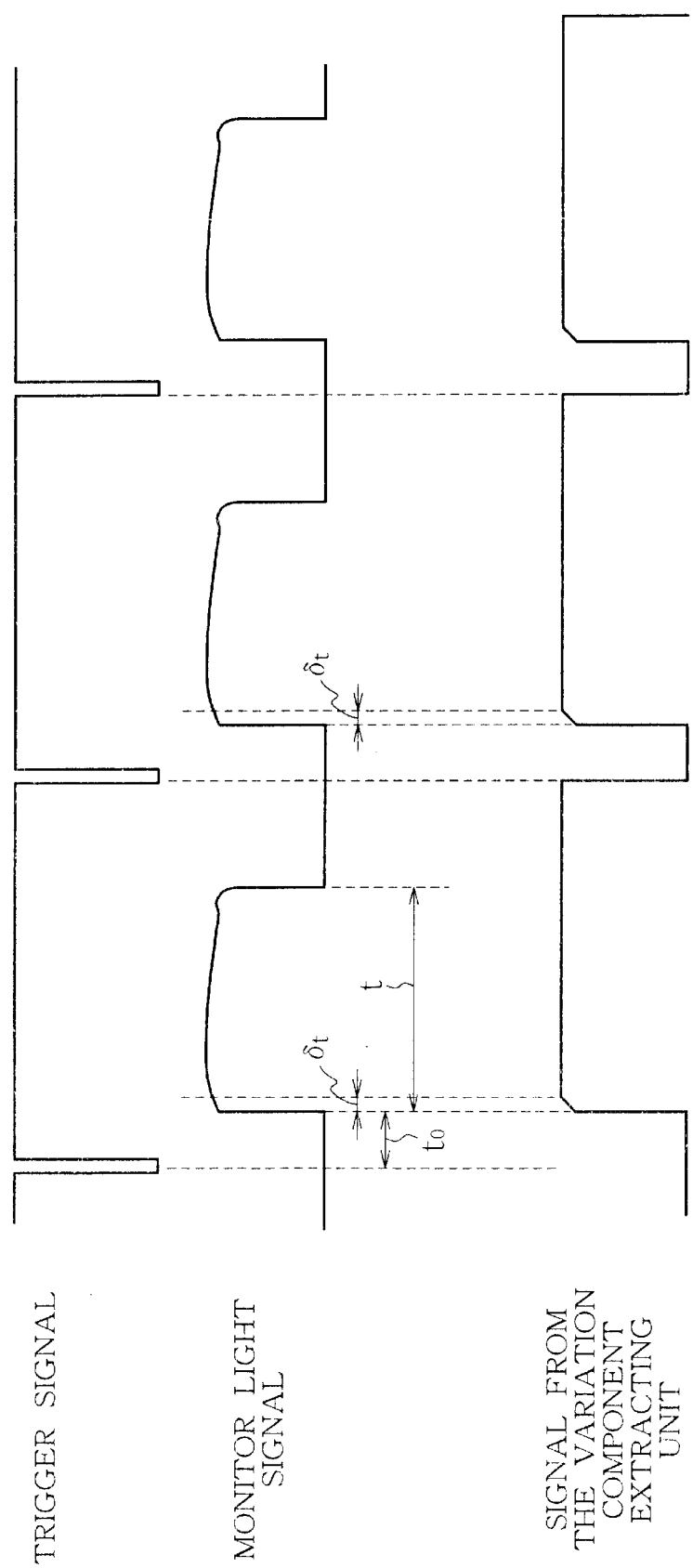
FIG. 4 is a timing chart showing an operation example of the waveform adjusting process shown in FIG. 1.

With reference to FIG. 4, when the trigger signal Trig being a reference to start scanning in the primary scanning direction is inputted, the waveform shaping unit 2 first stands-by for a constant retardation time to until the monitor signal rises. When the monitor signal rises, the waveform shaping unit 2 starts peak detection in to from triggering. This peak detection period is δt in the example shown in FIG. 4. The waveform shaping unit 2 outputs the peak value within δt until next trigger signal. This δt is a period sufficiently smaller than the period t when the monitor signal is being outputted so that they are set to fulfill $0 \leq \delta t < t/1000$ for example. But, if the monitor signal value within δt is 0, a predetermined value not depending on the monitor signal is outputted. This serves to make it possible to output a predetermined value as divisor even if the monitor signal were delayed against the transmission detecting signal. This predetermined value may be for example a peak value of the last round.

Figure 5:
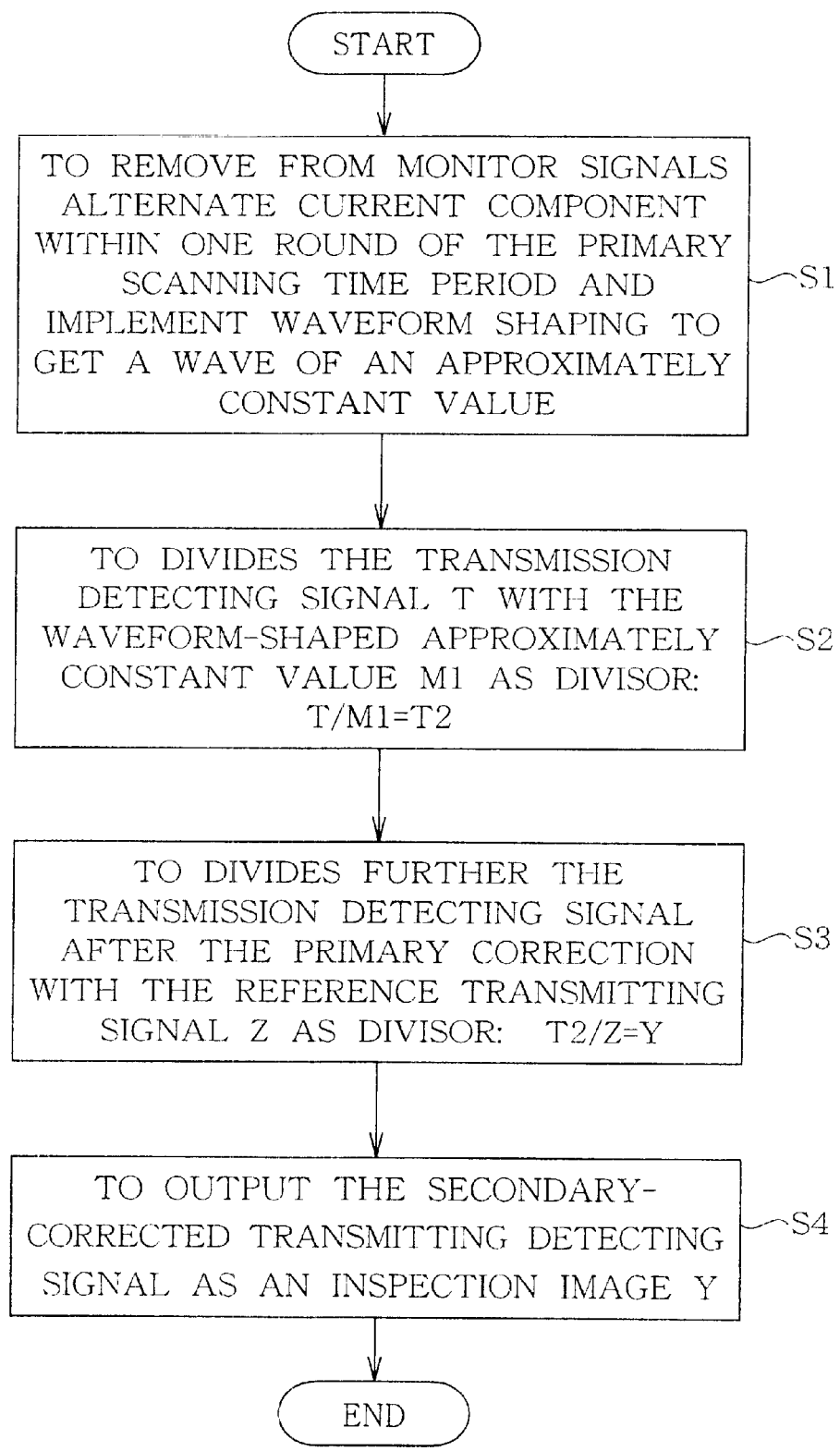
FIG. 5 is a flow chart showing an operation example of the device shown in FIG. 1 and FIG. 2.

Next, with reference to FIG. 5, the inspection process of the patterned shape inspection will be explained. First, the alternate current component of the monitor signals outputted from the monitor light detecting unit during a period when primary scanning takes place by the aforementioned scanning unit is removed for each of the primary scanning to be converted into the rectangular wave of an approximate constant value (Step S1). Subsequently, the aforementioned transmission detecting signal undergoes dividing with the rectangular wave as divisor group (Step S2). The divisor group includes a plurality of divisors. With reference to FIG. 4, when the monitor signal rises, the divisor value is increasing monotonously, to reach and remain at a constant value at δ and afterwards. Here, all of these successive values are called a divisor group. Subsequently, the transmission detecting signal having undergone dividing with the rectangular wave undergoes dividing with a predetermined reference transmitting signal as divisor group(Step S3). And the results of the division are outputted as an inspection image (Step S4).

With reference to FIG. 6, again a particular example of the patterned shape inspection is described. In the example shown in FIG. 6, three of transmission detecting signals and monitor detecting signals respectively due to three rounds of primary scanning having been implemented have been exemplified. For the first primary scanning, portions where patterns do not exist have been scanned and the transmission detecting signal Ta has been obtained. For the second primary scanning, there have been two patterns and transmitting have been implemented on three spots. As a result, the transmission detecting signal Tb is obtained. For the third primary scanning the portions where any pattern does not exist have been scanned and the transmission detecting signal Tc has been obtained. Because of transmitting a pattern, the transmission detecting signal Tb for the second round is tripartite, but the corresponding monitor detecting signal Mb for the second round is shaped an integral waveform since the signal has not transmitted the pattern. Vertical lines corresponding with the pattern shape have been described in the monitor detecting waveform for this second round.

The difference between the waveform of the monitor detecting signal and the wave-form of the transmission detecting signal reflects the components due to difference between the component as a result of transmitting through the glass surface of the reticle and the component due to the light paths being different. In Japanese Patent Laid-Open No. A-11-185041 specification, an example is disclosed wherein after the inspection light is divided as in the present invention, the transmitting light undergoes division with the monitor light. However, the invention described in this Japanese Patent Laid-Open No. A-11-185041 specification, cannot remove this influence of the noises due to the component as a result of transmitting through the glass surface of the reticle and the component due to the light paths being different. On the other hand, in the present invention, using the monitor signal M, only the levels of transmission detecting signal are corrected, and subsequently the waveform of the transmission detecting signal is corrected with the transmitting reference signal already measured in advance, thus, it is possible to remove this influence of the noises due to the component as a result of transmitting through the glass surface of the reticle and the component due to the light paths being different. In the example shown in FIG. 6, it is emphasized that a fracture Mc1 has occurred in the trailing edge of the detecting signal Mc monitoring by the primary scanning of the third round. When such a fracture occurs, in the above-described Japanese Patent Laid-Open No. 11-185041 specification, correction will not be implemented well.

Although there might be difference in levels between the transmission detecting signal T and the transmission detecting signal Z of the glass surface at the time when inspection undergoes, the waveforms are almost same. On the other hand, although there might be difference in waveforms between the transmission detecting signal and the monitor detecting signal, the levels are almost same. In the example shown in FIG. 6, it emphasized that optical intensity of the inspection light has been the normal optical intensity for the primary scanning of the first round, and has dropped for the primary scanning of the second round, and has increased for the primary scanning of the third round.

In advance, prior to obtaining the inspection image, the inspection light 20b, which has transmitted the transparent portion of the reticle 23, has been detected, and that detected data has undergone analog/digital (A/D) conversion with the A/D converter 6, and this is stored in the image memory 4 as the reference transmitting signal Z being digital information.

Next, at the time of obtaining the inspection image, at the same time when the transmission detecting signal T is obtained, the inspection light containing the variation component T1 of the optical intensity prior to arrival at the reticle 23 is photo-detected and obtained as the monitor signal M.

Next, using the waveform shaping unit 2, the variation information contained in the monitor signal M, that is, the optical intensity variation component T1 of the monitor signal M is removed, and the rectangular-shaped wave M1 with average value of the monitor signal is outputted as the voltage variation.

Next, using the divider 1, the transmission detecting signal T is divided by the rectangular-shaped monitor signal M1 outputted from the waveform shaping unit 2 as divisor, thus the transmission detecting signal T is standardized into a constant range of intensity (that is, gradation range). And, this transmission detecting signal T2 subject to the first correction is outputted.

Next, using A/D converter 3, the transmission detecting signal T2 outputted from the divider 1 after the first correction undergoes A/D conversion processing, and the transmission detecting signal T2 is outputted as digital signal.

Lastly, using the image dividing-calculation unit 5, based on the reference transmitting signal Z stored in the image memory 4, the transmission detecting signal T2 primary-corrected by the divider 1 undergoes dividing processing, and the inspection image (digital signal) Y in which distortion due to unevenness of the optical intensity of the transmission detecting signal T2 is corrected is generated.

Figure 6:
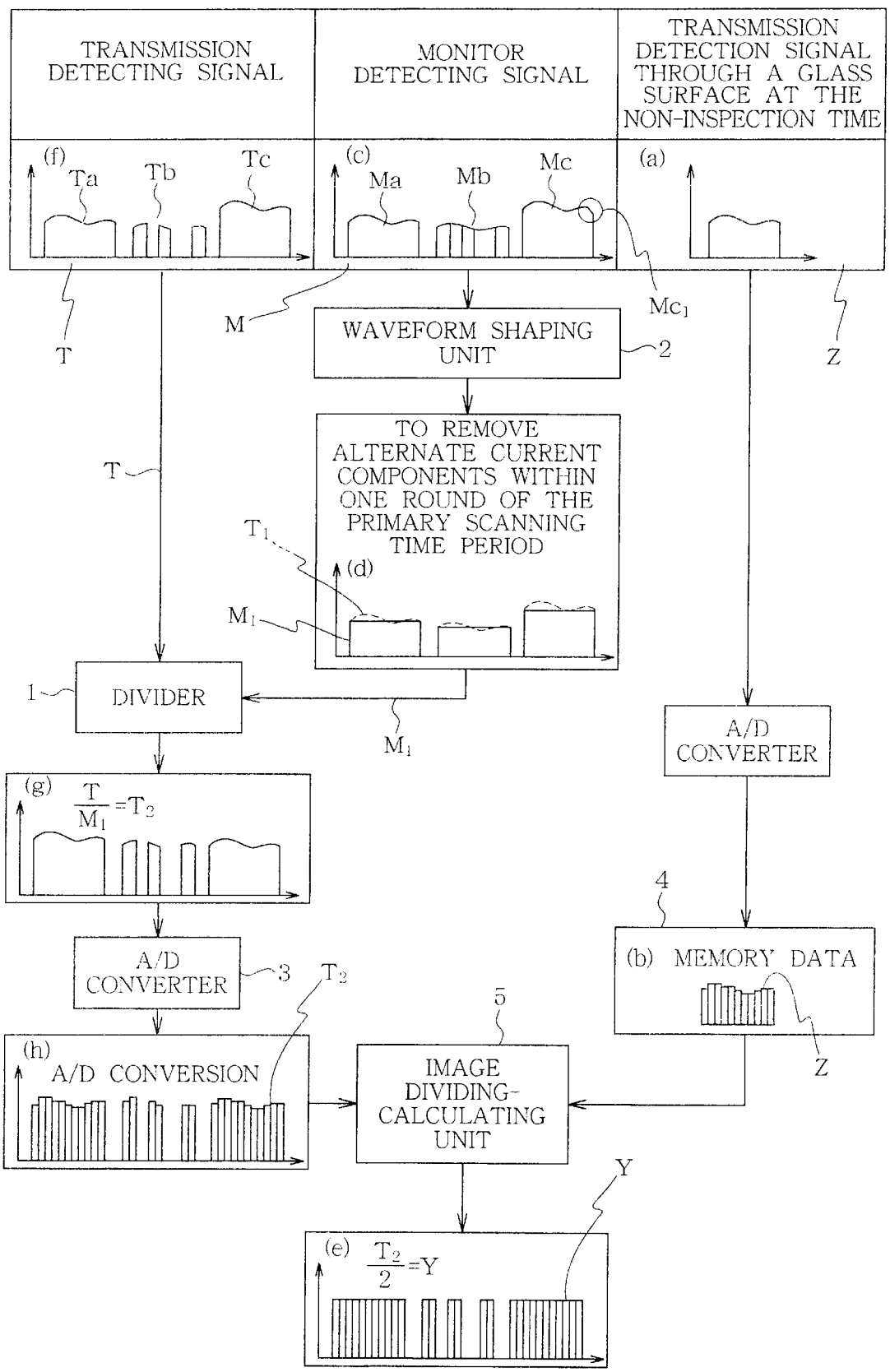
FIG. 6 is an explanatory graphs showing example of waveforms each configuration element shown in FIG. 1 and FIG. 2.

As shown in FIG. 6(g), division is implemented by the divider 1, the transmission detecting signal is standardized on a constant level. This serves to correct the level variation of the transmission detecting signal based on the optical intensity changing in the sub-scanning direction. At this time, since the waveform shaping unit 2 has shaped the monitor signal into the rectangular waves, the alternate current component of the transmission detecting signal, that is, the waveforms shown in FIGS. 6 (f) and (g) have not undergone changes. Subsequently, when division is implemented in the image dividing-calculation unit 5, as shown in FIG. 6(e), the alternate current components are removed. At this time, the alternate current component has not been merely removed, but has been corrected based on the transmitting reference signal Z, the noise due to transmitting through the glass surface of the reticle, the noise due to scanning direction of the inspection light, and the noise depending on the light path of the transmitting light can be exactly removed.

As described above so far, according to the present embodiment, not only the level variation because of variations due to the lapse of years of the optical intensity of the transmission detecting signal is corrected by the first correction unit, but also the component due to the variation of the optical intensity occurred within the primary scanning direction is corrected by the second correction unit, thus unevenness of the optical intensity causing dispersion of the image quality of the detection image can be corrected, and the image quality of the inspection image can be improved. In addition, since the monitor signal is shaped into the rectangular-shaped wave, the frequency of the monitor signal waveform is extremely low, and as a result of the frequency characteristics of the divider, deterioration of signals due to the dividing-calculation processing due to the frequency characteristics of the divider does not take place, and consequently, the divider can be obtained at comparatively low costs.

Next, an example, in which the first correction is implemented based on digital signals, is described.

Figure 7:
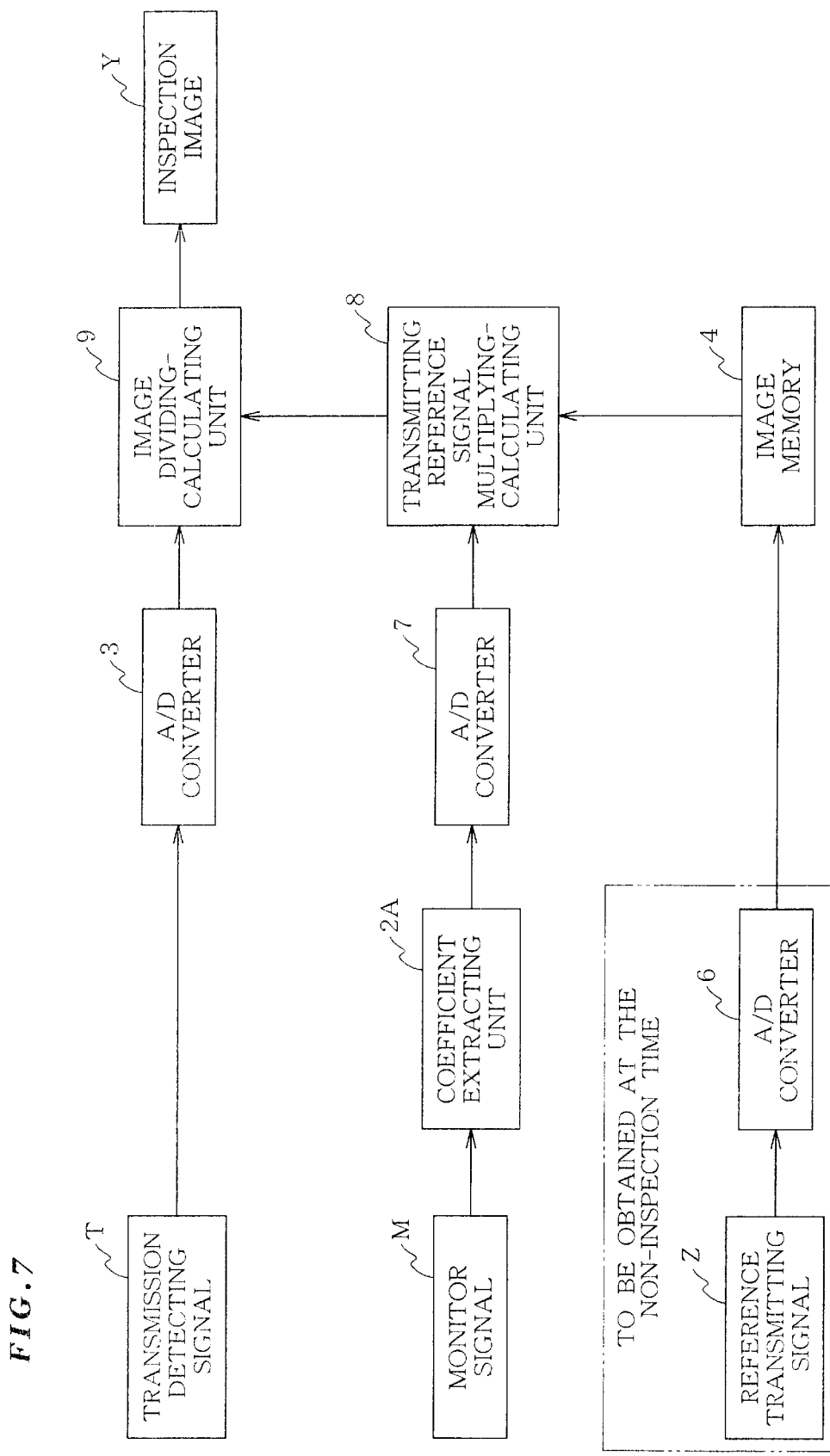
FIG. 7 is a block diagram showing a configuration example to implement the first correction with digital data.

With reference to FIG. 7, in replacement of the divider 1, a transmitting reference signal multiplying unit 8 implementing multiplying-calculation with digital data is comprised. In addition, as one mode of the waveform shaping unit 2, the coefficient extracting unit 2A to extract coefficients from the monitor signals is comprised. The coefficient extracting unit is, for example, a peak hold circuit operating in accordance with the timing chart shown in FIG. 4. The A/D converter 7 converts this peak value into digital data. At this time, the coefficient extracting unit 2A may be configured to output the peak value only within a predetermined short time period $\delta t2$, and the A/D converter 7 may be configured to digitize the data only within this $\delta t2$. That is, in the example shown in FIG. 7, it will be enough if only one value of the monitor signals is obtained. The transmitting reference signal multiplying unit 8 multiplies the value of the value M2 within a short time period of the monitor signal M by the value of the transmitting reference signal. That is, $M2 \times Z = Z1$ is executed. At this time, compared with multiplying by scattered values of the monitor signal, the calculation time period is short, and the memory capacity is less required. The image dividing-calculation unit 9 implements dividing-calculation of the transmission detecting signal as in the case shown in FIG. 1. The divisor at this time is the transmitting reference signal Z1 multiplied by the coefficient M2.

Figure 8:
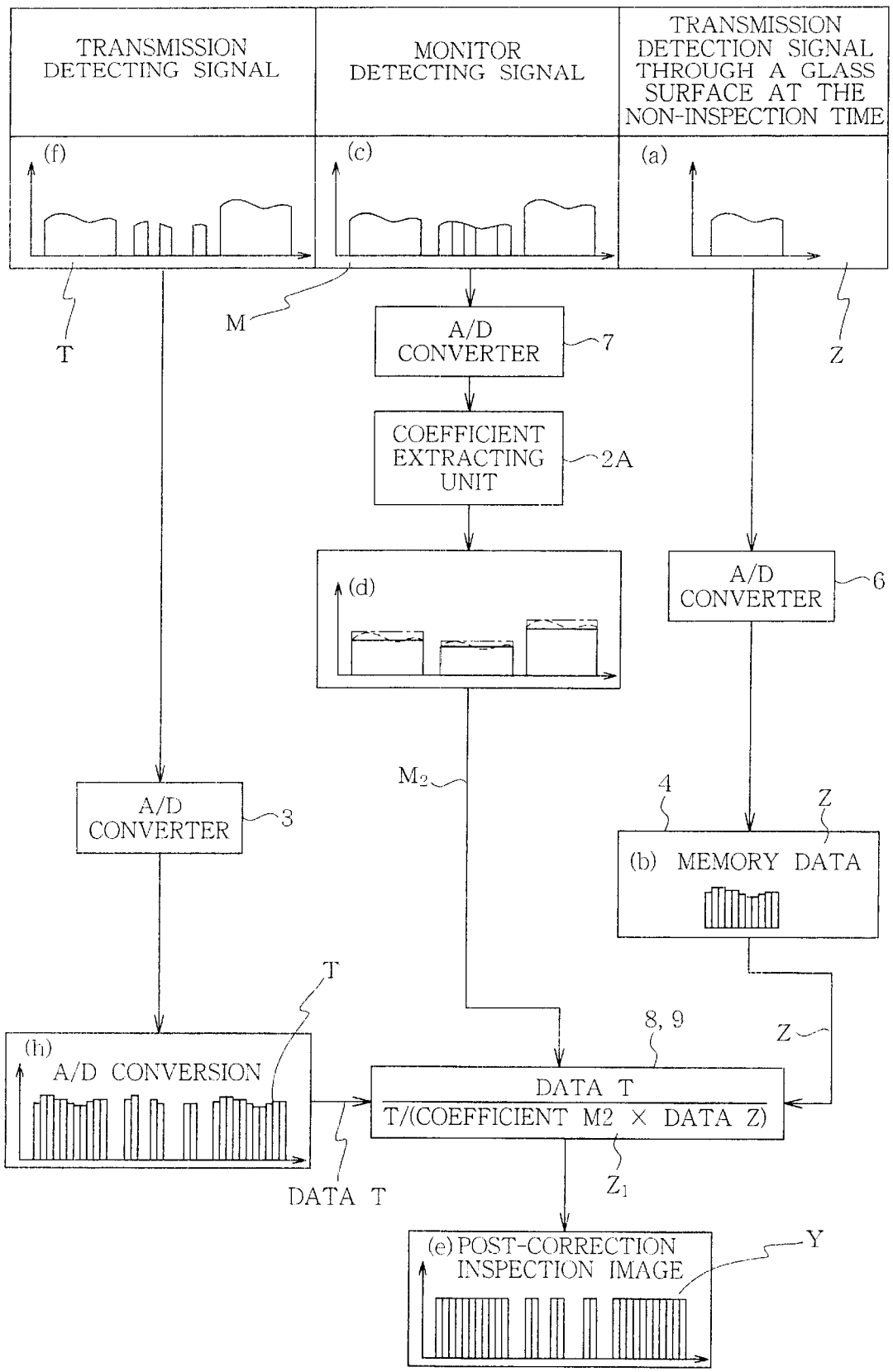
FIG. 8 is a block diagram showing a configuration example to obtain the feature values of monitor signals from digital data.

FIG. 8 shows a configuration to extract the coefficient M2 after the monitor detecting signal has been converted into digital data. In the example shown in FIG. 8, no processing on a real time basis is implemented. In this case, the first correction unit 10 comprises an A/D converter 7 to convert the monitor signal into digital data, and a coefficient calculation unit 8 to calculate the feature values of the monitor data, having been converted with this A/D converter, within a single primary scanning time period and output them as divisor at the time of dividing-calculating the aforementioned transmission detecting signal. Based on the data of the monitor signal converted into digital data covering a single primary scanning, the coefficient calculation unit 8 calculates predetermined feature values such as its maximum value, an average value, and a mean value, etc.

In the example shown in FIG. 8, the transmission detecting signal T as well as the monitor signal M are converted into digital data respectively by the A/D converters 3 and 7. The transmission detecting signal T having undergone A/D conversion is temporarily stored in the not-shown memory as digital data. On the other hand, the coefficient extracting unit 2A calculates one value representing features of a plurality of the scattered values based on the transmission detection signals T covering a single primary scanning. Subsequently, the transmitting reference signal, which has been measured in advance and converted into digital data, is read out, and this transmitting reference signal Z is multiplied by the representative value M2 of the monitor signal as coefficient. Subsequently, the transmission detecting signal T undergoes division by this transmitting reference signal, which has been multiplied by M2, as divisor. Of course, the transmission detecting signal may be divided by the representative value M2 of the monitor signal, and furthermore by the transmitting reference signal. In addition, the representative value of the monitor signal may be a value which is made to represent a plurality of values in the primary scanning direction.

As described above so far, according to the embodiments of the present invention, only the variation component of the optical intensity contained in the monitor signal is extracted as quantifying information, and based on the extracted signal of the aforementioned quantifying information, the aforementioned reference transmitting signal undergoes multiplying processing, and the variation-correction information synthesizing image is generated, and based on the aforementioned variation-correction information synthesizing image, the aforementioned transmission detecting signal undergoes dividing-calculation processing, and the inspection image having undergone removal of distortion and variation components for a short time period, and therefore, the waveforms of the transmission detecting signal and the monitor signal does not depend on frequencies, and not only the frequency characteristics do not limit the operation speed, but also the image processing can be executed in a concentrated manner, and thus in the case where the image processing performance is high, effectiveness will become attainable as an advantage.

As described above so far, according to the present invention, the transmission detecting signal based on the inspection light which has transmitted the transparent portion of the reticle at the time of inspection undergoes division based on the variation portion of the optical intensity contained in the monitor signal, and the variation portion of the optical intensity for a short time period at the time of inspection is removed from the transmission detecting signal for the primary correction, and subsequently, that transmission inspection signal subject to the primary correction undergoes dividing-calculation processing based on the reference transmitting signal based on the inspection light which has transmitted through the transparent portion of the reticle prior to obtaining the inspection image, and therefore, distortions resulting from variations of the optical intensity of the transmission detecting signal due to the lapse of years can be corrected, and in addition, the component reflecting variations of the optical intensity in a short time period due to illumination uniformity can be corrected, and unevenness of the optical intensity resulting in dispersion of the image quality of the inspection image can be corrected, and the image quality of the detection image can be improved.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 10-347148 (Filed on Dec. 7$^{th}$, 1998) including specification, claims, drawings and summary are incorporated herein by reference in its entirety.

What is claimed is:

1. A pattern shape inspection device comprising:
   a light source for irradiating inspection light;
   a scanning unit for scanning the inspection light;
   an inspection light dividing unit for dividing the inspection light scanned by the scanning unit into plural parts;

a monitor light detecting unit for receiving a first of the inspection lights divided by the inspection light dividing unit and converting the first part of the inspection lights into a monitor signal;

a transmitting light detecting unit for receiving a transmitting light, which has transmitted through a pattern shape, a second part of the inspection light divided by the inspection light dividing unit, and converting the transmitting light into a transmission detecting signal;

a waveform shaping unit for removing an alternate current component, within a primary scanning time period of the scanning unit, of monitor signals outputted from the monitor light detecting unit at each round of the primary scanning to convert the monitor signals into a rectangular-shaped wave of an nominally constant value;

a first correction unit for dividing the transmission detecting signal by the rectangular-shaped wave which has undergone shaping in the waveform shaping unit; and a second correction unit for dividing the transmission detecting signals corrected in the first correction unit with predetermined reference transmitting signals as a divisor group and outputting the results of said division as an inspection image.

2. The pattern shape inspection device according to claim 1, wherein the second correction unit comprises an image memory having memorized a reference transmitting signal corresponding with the transmitting light which has traveled along the same light path as that of the transmitting light and has transmitted through a reference pattern shape which does not have any patterned unit in the pattern shape.

3. The pattern shape inspection device according to claim 1, wherein the waveform shaping unit has comprised a peak hold circuit which outputs a peak value throughout a predetermined primary scanning time period immediately after the primary scanning of the inspection light starts.

4. The pattern shape inspection device according to claim 1, wherein the first correction unit has comprised a divider circuit to which the monitor signal and the transmission detecting signal as aforementioned are inputted in an analog signal and which divides the transmission detecting signal by the monitor signal.

5. The pattern shape inspection device according to claim 1, wherein the first correction unit has comprised a coefficient calculating unit to output feature values of monitor signals as divisors when the transmission detecting signal undergoes dividing-calculation.

6. A method for inspecting a pattern shape, in use of a pattern shape inspection device including a light source for irradiating inspection light, a scanning unit for scanning the inspection light, an inspection light dividing unit for dividing the inspection light scanned by the scanning unit, a monitor light detecting unit for receiving one of the inspection lights divided by the inspection light dividing unit and converting the one of the inspection lights into a monitor signal, and a transmitting light detecting unit for receiving a transmitting light, which as transmitted through a pattern shape, among the other inspection lights divided by the inspection light dividing unit and converting the transmitting light into a transmission detecting signal, the method comprising the steps of;

removing an alternate current component, within a primary scanning time period of the scanning unit, of monitor signals outputted from the monitor light detecting unit at each round of the primary scanning to convert the monitor signals into a rectangular-shaped wave of a nominally constant value;

dividing the transmission detecting signal by the rectangular-shaped wave; and dividing the transmission detecting signals which have undergone division by the rectangular-shaped wave with predetermined reference transmitting signals as a divisor group and outputting the results of said division as an inspection image.

7. The method for inspecting a pattern shape according to claim 6, wherein moreover the reference transmitting signal is generated based on the transmitting light which has traveled along the same light path as that of the transmitting light and has transmitted through a reference pattern shape which does not have any patterned portion in the pattern shape.

8. The pattern shape inspection method according to claim 6, wherein the process of implementing the rectangular-shaped wave comprises a process of outputting a peak value throughout a predetermined primary scanning time period immediately after the primary scanning of the inspection light starts.

9. A pattern shape inspection device comprising;

means for dividing an inspection light with which an inspection object undergoes scanning;

means for obtaining monitor signals corresponding with intensity changes of one of the divided inspection lights;

means for obtaining transmission inspection signals corresponding with intensity changes of the transmitting light having transmitted the inner-inspection object among the other part of the divided inspection lights;

means for extracting the direct current component of the monitor signals, means for correcting the variation of intensity of the inspection light in the sub-scanning direction with the value for this direct current component; and means for correcting the variation of intensity of the transmitting light in the primary scanning direction with the predetermined reference transmitting signals.

10. A. pattern shape inspection device comprising:

means for dividing an inspection light with which an inspection object undergoes scanning;

means for obtaining monitor signals corresponding with intensity changes of one part of the divided inspection light;

means for obtaining transmission inspection signals corresponding with intensity changes of another part of the divided inspection light transmitted through the inspection object;

means for extracting the direct current component of the monitor signals;

means for correcting a predetermined reference transmitting signals corresponding with the variation of intensity in the sub-scanning direction; and means for correcting the variation of intensity of the transmitting light with a corrected reference transmitting signals.

* * * * *